US006288539B1

(12) United States Patent
Ellis (10) Patent No.: US 6,288,539 B1
(45) Date of Patent: Sep. 11, 2001

(54) SYSTEM FOR MEASURING AN EMBRYO, REPRODUCTIVE ORGANS, AND TISSUE IN AN ANIMAL

(75) Inventor: James S. Ellis, Broomfield, CO (US)

(73) Assignee: Pheno Imaging, Inc., Broomfield, CO (US)

(*) Notice: Subject to any disclaimer, the term of this patent is extended or adjusted under 35 U.S.C. 154(b) by 0 days.

(21) Appl. No.: 09/560,422

(22) Filed: Apr. 27, 2000

Related U.S. Application Data (63) Continuation-in-part of application No. 09/151,234, filed on Sep. 10, 1998, now Pat. No. 6,084,407.

(51) Int. Cl.[7] .................................................. G01V 3/00
(52) U.S. Cl. ............................................. 324/300; 600/443
(58) Field of Search ........................... 324/300; 600/443; 128/660

(56) References Cited

U.S. PATENT DOCUMENTS

| 4,654,593 | 3/1987 | Ackerman | 324/300 |
|---|---|---|---|
| 4,668,457 | 5/1987 | Nakai et al. | 324/322 |
| 5,339,815 | 8/1994 | Liu et al. | 128/654 |
| 5,398,290 | 3/1995 | Brethour | 324/300 |
| 5,483,441 | 1/1996 | Scofield | 324/300 |
| 5,512,825 | 4/1996 | Atalar et al. | 128/654 |
| 5,520,183 | 5/1996 | Lake et al. | 324/300 |
| 5,613,493 | 3/1997 | Schafer | 128/660.06 |
| 5,673,647 | 10/1997 | Pratt | 119/1.02 |
| 5,836,880 | 11/1998 | Pratt | 600/443 |
| 6,084,407 | * 7/2000 | Ellis | 324/300 |

OTHER PUBLICATIONS

Doyle E. Wilson Et Al., Scanning Into the Future, Department of Animal Science, Jan. 1, 1998, Publisher: Iowa State University, Published in: Ames, Iowa.

H. Ville et al., An Evaluation of Ultrasound and Nuclear Magnetic Resonance Spectroscopy to Measure in Vivo Intramuscular Fat Content of, Journal of Animal Science, Jan. 1, 1997, pp. 2942–2949.

* cited by examiner

*Primary Examiner*—Jay Patidar
*Assistant Examiner*—Brij B. Shrivastav
(74) *Attorney, Agent, or Firm*—James R. Young (57) ABSTRACT

A computerized system that scans the animal using Magnetic Resonance Imaging (MRI). The scan data is analyzed within the computer to determine if an embryo is present or to determine if scar tissue is present, or to determine the size of organs within the animal. The scan data is produced as digital pixel values, coded as gray scale values, within scan wave lines wherein the gray scale values represent types of tissue. The size of the embryo is defined by separating the embryo tissue from the surrounding muscle tissue of the uterus. The embryo is classified by size by comparing and ranking within like kinds of animals to determine the age of the embryo.

19 Claims, 9 Drawing Sheets

SYSTEM FOR MEASURING AN EMBRYO, REPRODUCTIVE ORGANS, AND TISSUE IN AN ANIMAL

CROSS REFERENCE TO RELATED CASES

This application is a Continuation-in-Part of application Ser. No. 09/151,234 of James S. Ellis, filed Sep. 10, 1998, now U.S. Pat. No. 6,084,407 entitled "System for Measuring Tissue Size and Marbling in an Animal."

FIELD OF THE INVENTION

This invention relates to animal measuring systems and more particularly to measuring an embryo within the animal, a mammary gland, testicles and other body parts of the animal. Even more particularly, the invention relates to measuring the embryo within the animal, mammary glands, testicles and other body parts through Magnetic Resonance Imaging systems.

BACKGROUND OF THE INVENTION

In modern times it has been very important for domestic livestock producers to determine if individual cow's reproductive organs are healthy and if the cow is or is not pregnant. Just as importantly, is the need to know if the bulls reproductive organs are able to maintain maximum fertility. It is also important to know if other areas of the animal are healthy such as the milk secretion cells of the mammary glands, the digestive tract, lungs, heart, skeleton and even teeth. Each of these body parts are directly related to the productivity and reproductivity of the animal. The function of each of these body parts is directly related to the very economic base of maintaining a profitable herd. They become even more important when the animal is sold for breeding stock or as a production unit for another herd.

There have been several means to measure the embryo in the pregnant cow. For many years a skilled veterinarian or technician could palpate the uterus of the cow and determine at 70 to 90 days if an embryo (about the size of a golf ball) was present. Ovaries could also be palpated to detect healthy functions or problems such as a cyst. Some prior art systems use ultra-sound to detect an embryo. These methods have several drawbacks. Both require a skilled technician and on occasion the method of palpation can cause harm to the cow or even dislodge the embryo causing an abortion.

The mammary glands or udder of the dairy cow is extremely important to the productivity of the cow. Several diseases such as mastitis can cause severe scar tissue within the milk secretion cells of the udder. Also, any severe blow to the mammary glands, such as a kick from another cow can cause scar tissue. Once scarred, the milk secretion cells fail to produce milk causing the cow's production to drop drastically. A teat canal can also be damaged preventing the milk flow from the milk secretion cells to exit the udder through the teat. If one or two of the four mammary glands are totally damaged, the cow is often culled from the herd because milk production can be reduced by 25 to 50 percent. Some prior methods have had limited success in determining the amount of scar tissue in an udder or teat. Palpation will detect the presence of scar tissue but cannot determine the amount of scar tissue deep within the mammary gland. Other prior art systems such as ultra-sound using a skilled technician can detect the presence of scar tissue. However, the "speckle" found in the ultra-sound scanning can make it very difficult to accurately measure the actual amount or percentage of scar tissue.

Modern research has shown that there is a positive correlation to the circumference of the bulls testicles and the bulls future fertility. The larger circumference when measured at a young age adds value to the future fertility of the bull. The current means for measuring the testicles is very slow, wherein a soft tape measure is used to simply encircle the testicles at the largest diameter. Again, the accuracy is dependent on the technician and no measurement is taken of the sperm producing cells within the testicles.

Additionally, there is a need to measure, evaluate and compare numerous damaged or unhealthy animal body parts with those that are healthy such as vital organ tissue, digestive tract tissue, respiratory tract tissue, cardiovascular system tissues, skeletal tissue, bone joints, ligaments, tendons, teeth and horns (or antlers). There is on occasion a similar need to evaluate any of the above animal body tissue of the carcass of an animal. Current methods have several drawbacks including inaccuracy, lack of speed, inability to diagnose without surgery and often the need of a skilled technician.

It is thus apparent that there is a need in the art for an improved method or apparatus which provides information about an embryo within the animal, milk secretion cells, testicles, and other vital animal body parts while increasing the speed, eliminating the inaccuracies of palpation, while reducing the skill required to operate the system. The present invention meets these and other needs in the art.

SUMMARY OF THE INVENTION

It is an aspect of the present invention to provide information about an embryo and reproductive tract inside a female animal.

It is another aspect of the invention to provide information about the milk secretion cells within the mammary glands of the udder of an animal.

Another aspect of the invention is to provide the circumference, diameter, and the size of the testicles of a male animal.

A further aspect of the invention is to measure, evaluate and compare many of the animal's body parts to determine the health or damage of those body parts.

The above and other aspects of the invention are accomplished in a computerized system that scans the animal using Magnetic Resonance Imaging (MRI). The scan data is analyzed within the computer to determine if an embryo is present. The scan is further analyzed to determine the size of the embryo in the early stages of pregnancy, as early as 25 to 30 days into the pregnancy.

The scan data is produced as digital pixel values within scan wave lines. Multiple rapid scans of scan wave lines can be used to create real-time images. The pixel values are coded as gray scale values wherein the gray scale values of each pixel is representative of the type of tissue scanned. The computer system thus classifies each pixel, based upon its gray scale value, muscle, cartilage, ligament, tendons, fat, skeletal tissue, bone joints, scar tissue, vital organ tissue, reproductive tract tissue, teeth, horns, antlers, etc.

Once classified, the pixel data can be presented on the screen of the computer system. The diameter and the circumference of the embryo can be defined by separating the embryo tissue from the surrounding muscle tissue of the uterus. Once the circumference of the embryo tissue is defined for a particular animal, the embryo can be classified by size by comparing and ranking within like kinds of animals to determine the age of the embryo. As the embryo grows, the sex of the embryo can be determined. If no embryo is present then the animal is recorded as not pregnant.

Also, once the pixel data is classified from a scanned area such as the udder of a cow, the percentage of scar tissue in the mammary glands can be calculated when compared to the total amount of healthy milk secretion cells within the representative scanned wave lines.

The data from a scanned area such as the testicles of a bull can be used to calculate the diameter and circumference of the testicles by separating the testicle tissue from the surrounding skin tissue. Once the perimeter of the testicles is defined, the size and the density of the sperm producing cells can be calculated and an average of all wave lines representing each testicle can be calculated.

Once the embryo size, percentage of mammary gland scar tissue, testicle evaluations, or any other animal body parts have been determined for a particular animal, the animal is rated and classified for ranking within like kinds of animals.

BRIEF DESCRIPTION OF THE DRAWINGS

The above and other aspects, features, and advantages of the invention will be better understood by reading the following more particular description of the invention, presented in conjunction with the following drawings, wherein.

DESCRIPTION OF THE PREFERRED EMBODIMENT

The following description is of the best presently contemplated mode of carrying out the present invention. This description is not to be taken in a limiting sense but is made merely for the purpose of describing the general principles of the invention. The scope of the invention should be determined by referencing the appended claims.

Figure 1:
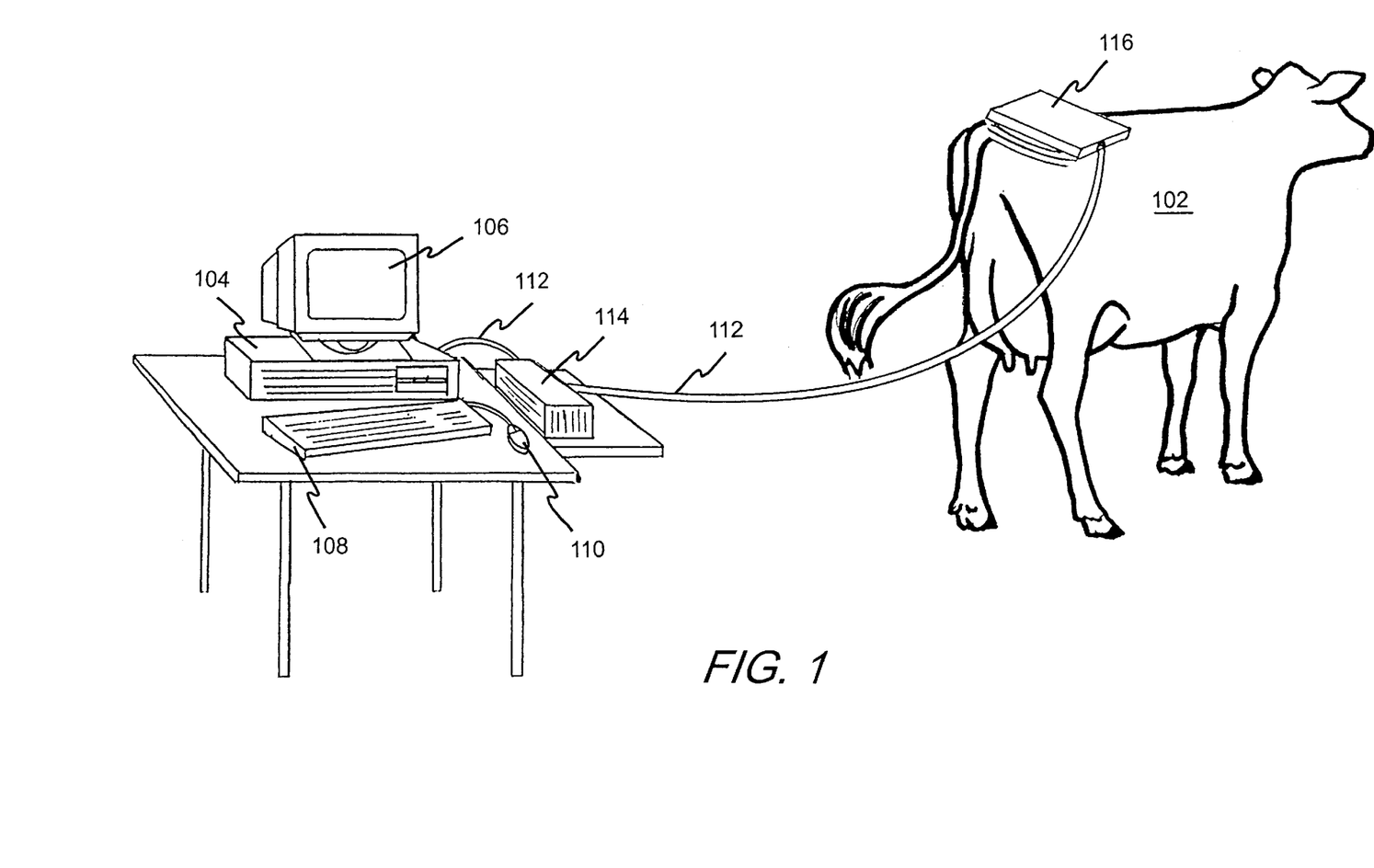
FIG. 1 shows a female animal (cow) being scanned in the pelvic area to detect an embryo using the present invention.

FIG. 1 shows a female animal (cow) 102 being measured using the present invention. Referring to FIG. 1, the animal could be in a chute, in a stanchion, standing at halter, or simply standing freely. A computer system 104 is shown having a display 106, keyboard 108 and mouse 110. This is a conventional personal computer system, which is commonly used. Cable 112 connects the computer system to the MRI scanner parts 114 and 116. Part 114 typically contains the electronics of the MRI scanner, and part 116 contains the scanning element that is placed over the animal in the pelvis area that is just above uterus tract. An example of this type of MRI system can be found in U.S. Pat. No. 5,304,930 entitled "Remotely Positioned MRI System", issued Apr. 19, 1994 to Crowley, et al.

The MRI scanning element 116 can be placed at several different locations over the animal 102, and precisely located as desired. Also, scanning element 116 or additional elements can be placed on a movable apparatus (not shown), controlled by the computer system 104, that allows the scanning element 116 or elements to be moved along desired area(s) of the animal to obtain the multiple scans needed to perform various body measurement(s), as described below. The scanning element 116 may be moved to locate the largest diameter of the uterus, thus allowing comparisons of the size of the uterus to typical sizes for the animal, or to compare the same animal scanned at different times.

Once the scanning element 116 is in place, the mouse 110, or other switch device (not shown), is used to start a scan, which is typically completed in a few seconds. Should the animal 102 move during the scan the operator can re-scan so as to get a correctly focused scan.

Once the scan is complete, computer system 104 analyzes the MRI wave lines to determine the desired measurements of the embryo size or various body parts located underneath the scanning element 116, as will be described below. After analyzing the embryo size and various body parts, the computer system 104 rates and classifies the animal to rank it with similar embryo and body parts of like kinds of animals.

As an alternative to producing digital data directly from the MRI scanning device, an MRI scan can produce a photographic media print or negative, which is then scanned and digitized using a conventional scanner. Additional scan lines could be produced, and the scan lines produced closer together, to scan any desired percentage of the embryo or other body part, up to 100 percent. Producing additional wave lines takes additional time, however, additional wave lines could be used to produce additional accuracy in the estimates of the embryo size and other body part measuring estimates. As more time is taken, to produce a higher number and/or density of wave lines, the probability that the animal will move increases, but a complete scan is possible if the animal does not move, which is possible for some docile animals or by restraining the animal. Also, when a MRI scan is performed, the distance between the scan wave lines is set within the MRI scanner, so the depth of the tissue scanned by the wave lines is therefore also adjustable.

Figure 2A:
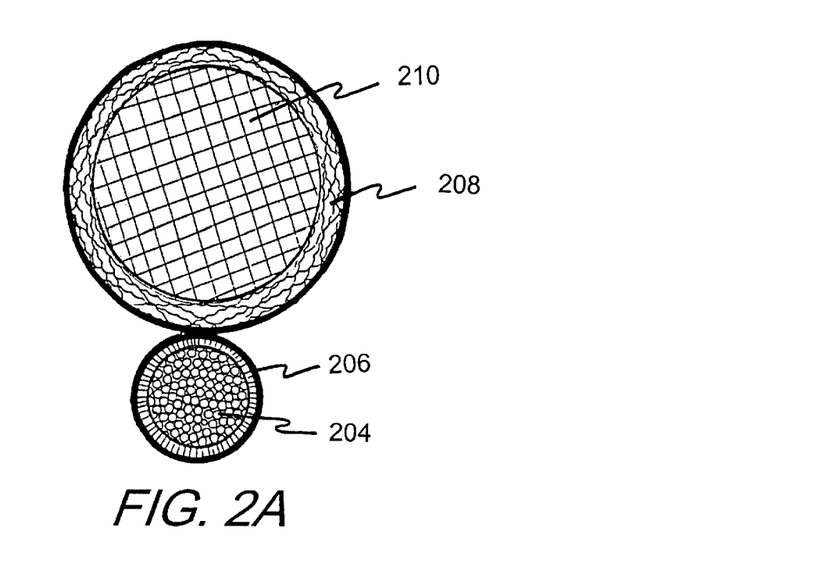
FIG. 2A show a cross-section of a dairy cow uterus below the colon.
Figure 2B:
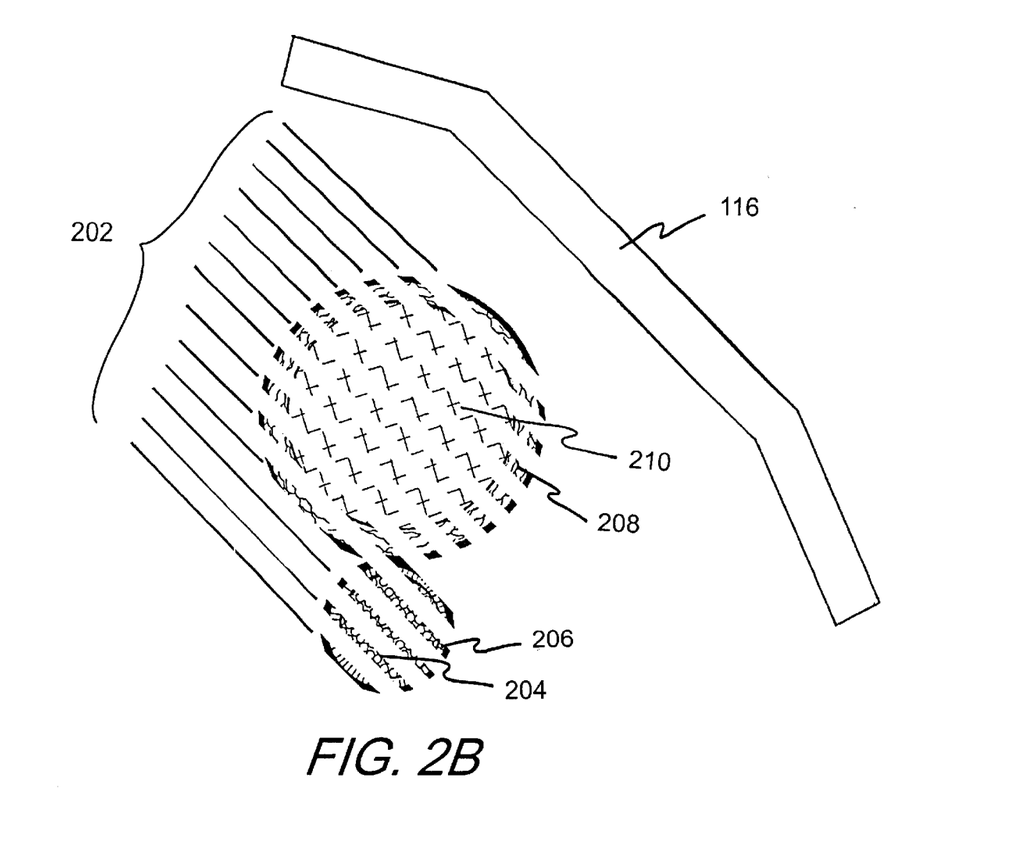
FIG. 2B shows MRI wave lines where an MRI scanner produces data of the texture of the embryo, uterus and colon tissue.

FIG. 2A shows a vertical cross-sectional view, and FIG. 2B shows the scan data of the view of FIG. 2A, which taken just behind the hook bone which is the large protruding bone that is located forward of the thurl bone and the forward most part of the pelvic region of the animal 102 (FIG. 1) and illustrates the location where the scan of the reproductive tract is typically taken in a cow. Only the uterus 206 surrounding the embryo 204 which is directly under the large intestine (colon) 208 is shown to more easily display the embryo 204. Other tissues such as the pelvic bones, body fat, and hide are not shown in order to simplify this drawing.

Referring to FIGS. 2A and 2B, the MRI scan, created from the scanner 116, produces a plurality of scan wave lines 202 which capture data about the embryo 204, and uterus 206 which is located below the colon 208. The colon 208 can be filled with feces 210. FIG. 2B shows the scan wave lines 202 that are returned to the computer system 104. The computer system locates the embryo 204 as a circular tissue surrounded by the circular uterus muscle 206, which is located just below the larger circular colon 208. Once the embryo 204 is located by the computer system then the diameter and circumference of the embryo 204 is calculated, thus the age of the embryo can be rated by comparing the size to predetermined size measurements of known embryo measurements of animals of like kind.

Figure 3:
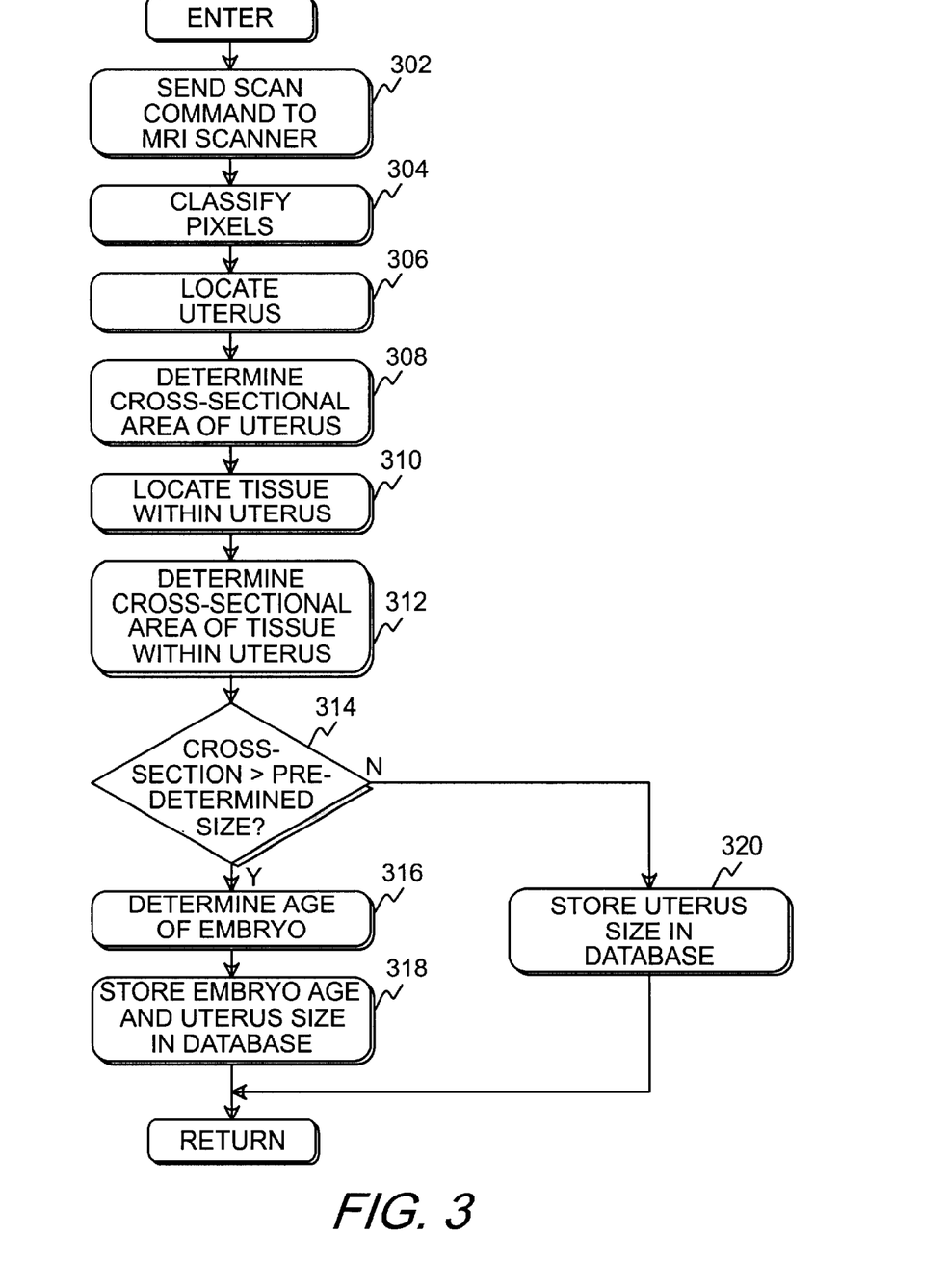
FIG. 3 shows a flowchart of detecting an embryo in the animal shown in FIGS. 1, 2A and 2B.

FIG. 3 shows a flowchart of the process of determining the size of an embryo in an animal, using the data of FIG. 2B. Referring to FIG. 3, after entry, step 302 sends a scan command to the MRI scanner 116 to cause it to perform a scan. The scanner has previously been placed over the back of the animal, in the vicinity of the reproductive system, as shown in FIG. 1. After scanning, the scanner returns the scanned data, as illustrated in FIG. 2B, in the form of pixels of information, and step 304 classifies the pixels into various types of tissue based on the grayscale value of each pixel. Alternatively, the MRI data can be processed before being converted into pixel data to determine a type of tissue.

Typically each of the pixels is returned as a gray scale level, and several pixels may be combined before analysis to produce a combined gray scale level. The gray scale level for each pixel is analyzed to separate each into a pixel that represents muscle tissue, a pixel that represents fat tissue, a pixel that represents cartilage, a pixel that represents skeletal tissue, etc., wherein the separation is based upon the range of gray scale levels typically found for each of the type of tissues within the type of animal scanned.

Once the pixels are classified, step 306 locates the uterus of the animal. As discussed above in FIGS. 2A and 2B, the uterus is located below the colon of the animal, wherein both the uterus and colon appear as circular sections of muscle, with the uterus being the smaller circular section. This process assumes that the scan occurs early in pregnancy when the uterus is still smaller than the colon. It would also be possible to scan an animal later in pregnancy and locate the uterus as the larger circular section of muscle. In either case, the uterus is located below the colon.

It may be possible that the uterus is not present in the scan, wherein the scanning device must be moved and a second, or subsequent, scan performed to locate the uterus. This can easily be done by viewing the scan on the display 106 of the computer system, before instructing the computer system 104 to analyze the scan data.

Once the uterus is located, step 308 calculates the cross-sectional area of the uterus. Step 310 then locates any tissue within the uterus by locating the inner muscular wall of the uterus and locating any tissue within the wall. Step 312 then determines the cross-sectional area of the tissue within the uterus. Step 314 then compares the size of the tissue to a pre-determined size of a small embryo.

Alternatively, pregnancy can be determined using a typical size for the uterus of an animal of the size of the animal being measured, or it can be done by measuring the animal periodically and keeping the size of the uterus at each measurement, wherein the size of the uterus in this measurement is compared to past measurements of this animal. This, of course, can only determine pregnancy once the embryo has achieved sufficient size to enlarge the uterus. This may require that the scanner be adjusted until the largest diameter of the uterus is displayed.

After determining the size of the tissue, step 314 transfers to step 316 if the animal is pregnant, and step 316 determines the age of the embryo from the size of the uterus and/or the size of the embryo within the uterus. Step 318 then stores the embryo age, size and uterus size in a database.

If the animal is not pregnant, step 314 goes to step 320 which stores only the uterus size in the database for later comparisons.

As a second alternative, pregnancy can be determined by examining the scan data to locate bone tissue with the uterus. This is possible once the embryo develops bone tissue. Since there is no bone tissue near this area of the animal, bone tissue can be easily located, and thus pregnancy easily determined, once the embryo develops some bone structure. Also, once the embryo has developed sufficiently, the sex of the embryo can be determined.

Figure 4:
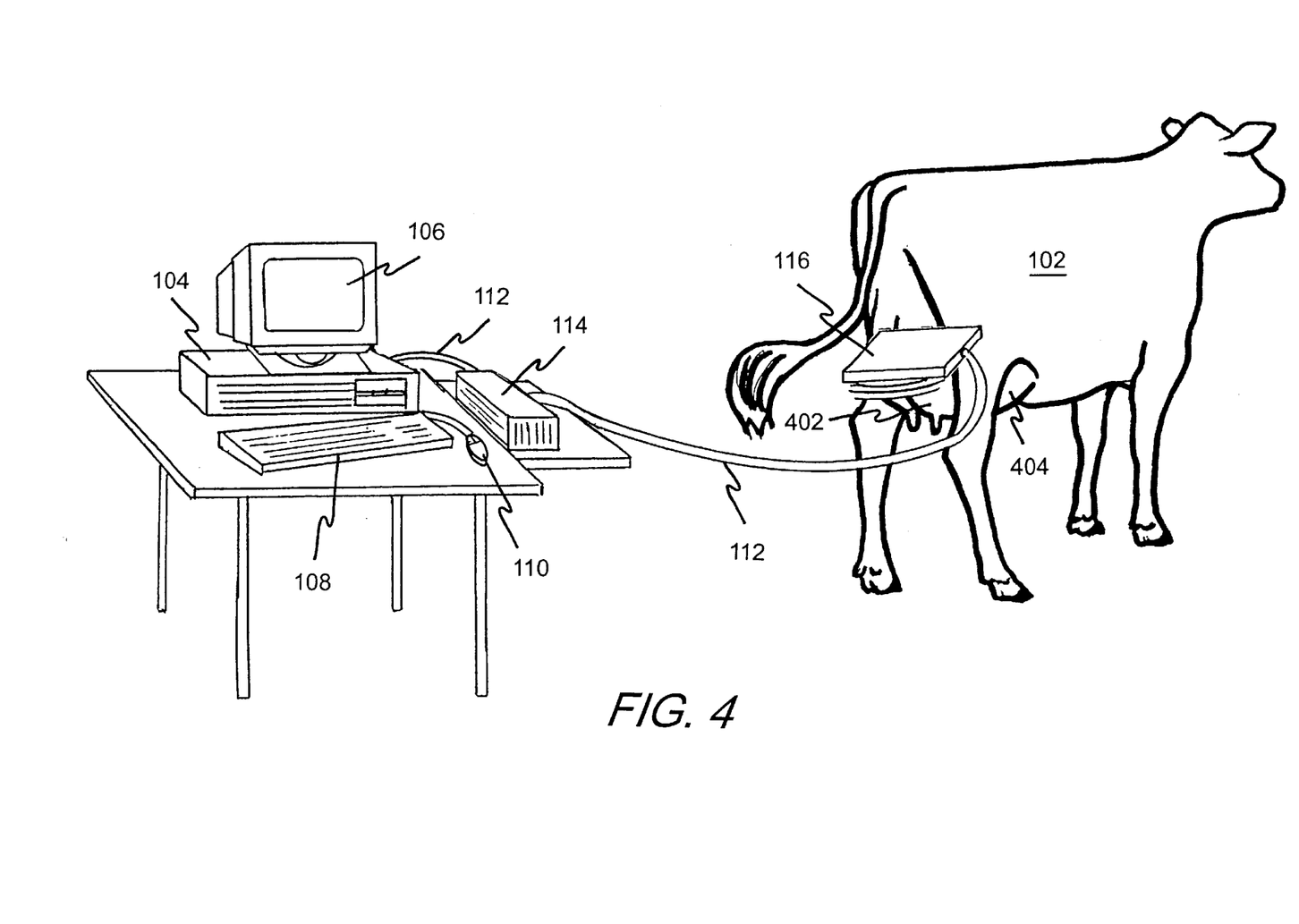
FIG. 4 shows an animal being scanned in the udder area to detect the scar tissue in the mammary glands using the present invention.

FIG. 4 shows a female animal 102 being measured in the rear udder (mammary) 402 area using the present invention. Referring now to FIG. 4, the same measuring system as described in FIG. 1 is used to measure the milk secretion cells in the udder. The measuring system includes additional processes, described below, to detect the milk secretion cells, scar tissue, membranes surrounding the mammary glands and the ligaments supporting the mammary. The udder contains four mammary glands. FIG. 4 shows the present invention scanning the rear two mammary glands, known as the rear udder 402. The two forward mammary glands known as fore udder 404 are located in front of the hind leg and attach to the under belly of the animal. The fore udder 404 can also be measured by the present invention by placing the scanning element 116 forward of the hind legs and using additional programs to detect the milk secretion cells in that area.

Figure 5A:
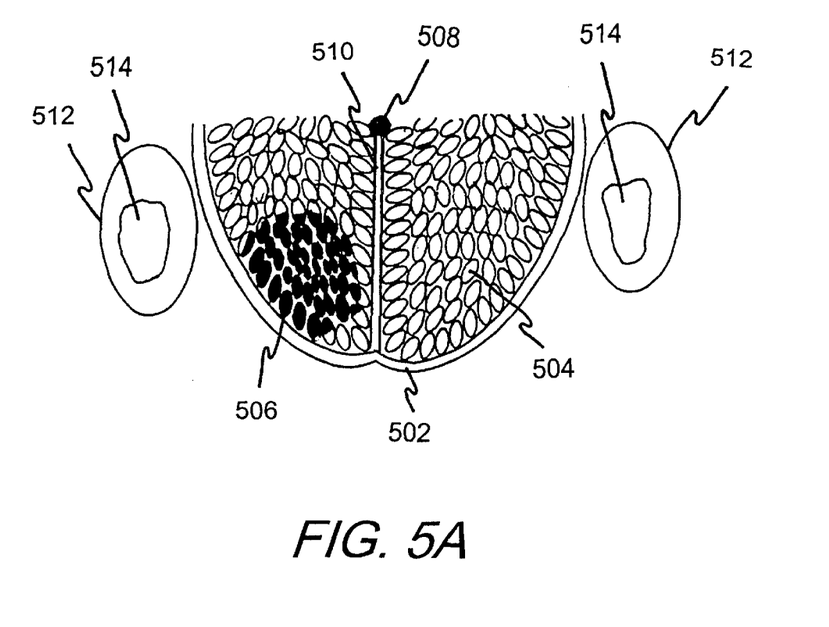
FIG. 5A shows a cross-section of the mammary glands.
Figure 5B:
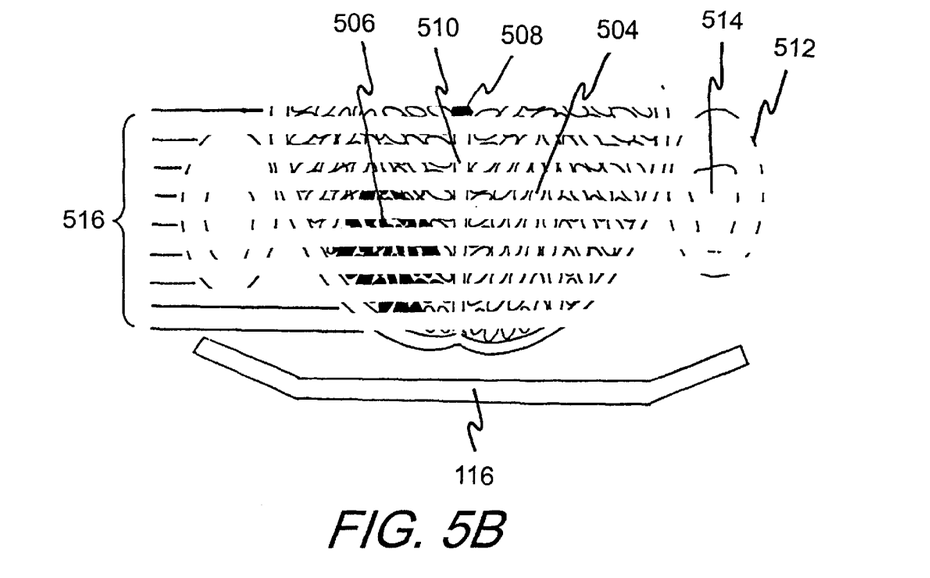
FIG. 5B shows MRI wave lines where an MRI scanner produces data of the scarred milk secretion cell tissue, and surrounding healthy milk secretion cells.

FIGS. 5A and 5B show a horizontal cross-sectional view, FIG. 5A, taken from the rear of the udder and illustrates the location, FIG. 5B, where the scan of the rear mammary glands is typically taken in the dairy cow. Referring now to FIGS. 5A and 5B, the MRI scan, created from the scanner 116, produces a plurality of scan wave lines 516 which capture data about the milk secretion cells 504 which are located within the udder skin 502. The numerous milk secretion cells 504 are located within both mammary glands that are separated by the mammary gland membranes 510. Known as scar tissue, the scarred milk secretion cells 506 are displayed in the scan wave lines 516 as different levels of gray than do the healthy milk secretion cells 504. Some milk secretion cells 504 can be partially damaged. The scar tissue cells 506 that are severely damaged are displayed in the scan wave lines 516 as smaller and appear tightly entangled when compared to the healthy milk secretion cells 504. The udder is held close to the animals body by the medial suspensory ligament 508 that is attached to the bottom or floor of the udder (all four mammary glands) and extends upward through the center of the udder to be attached to the pelvic cradle. Portions of the hind leg 512 and the hind leg tissue such as the leg bone 514 may appear in the scan wave lines 516 depending on the position of the hind legs 512 at the time of the scan.

Once the scan is complete, the computer system 104 analyzes, as described below, the MRI wave lines to determine the scar tissue 506 surface area. The scar tissue surface area is then compare to the surface area of all of the milk secretion cells 504 and scar tissue 506 within the individual mammary gland, and a percentage of scar tissue is then calculated. After analyzing the percentage of scar tissue, the computer system 104 rates and classifies the animal's udder to rank it with similar udders of like kinds of animals.

Figure 6:
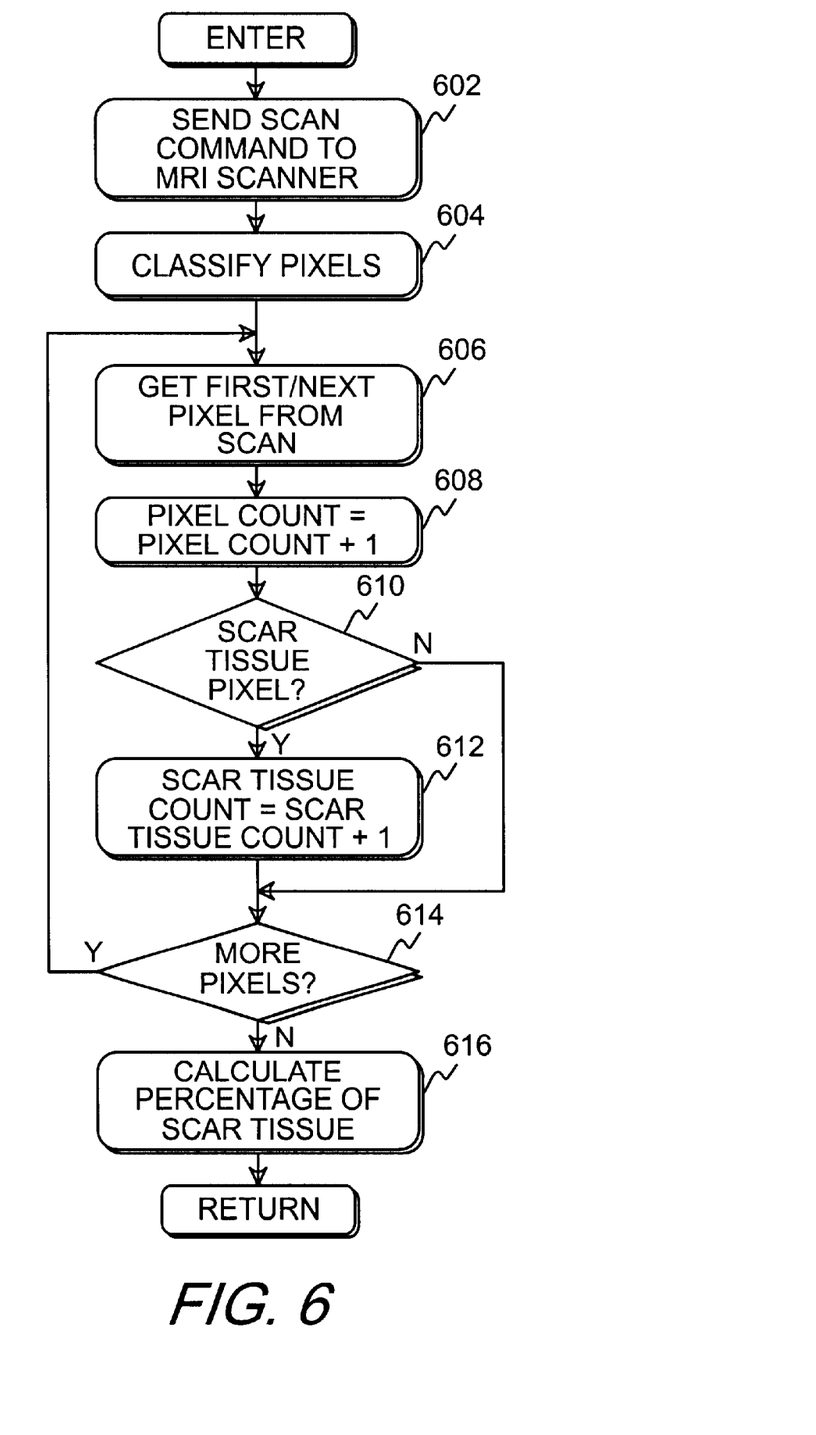
FIG. 6 shows a flowchart of the process of measuring a percentage of scar tissue in the animal scanned in FIGS. 4, 5A and 5B.

FIG. 6 shows a flowchart of the process of determining the percentage of scar tissue within the mammary system of the animal shown in FIGS. 4, 5A, and 5B. Referring to FIG. 6, after entry, step 602 sends a scan command to the MRI scanner 116 to cause it to perform a scan. The scanner has previously been placed at the back of the animal, in the vicinity of the mammary system, as shown in FIG. 4. After scanning, the scanner returns the scanned data, in the form of pixels of information, and step 604 classifies the pixels into various types of tissue based on the grayscale value of each pixel, as discussed above.

Step 606 gets the first, or next, pixel from the scanned data. Step 608 adds one to the count of pixels, and step 610 determines, from the grayscale value of the pixel, if the pixel represents scar tissue. If the pixel is scar tissue, step 610 goes to step 612 which adds one to the count of scar tissue pixels.

After adding one to the count of scar tissue pixels, or if the pixel did not represent scar tissue, control goes to step 614 which determines whether or not more pixels are available to process. If more pixels are available, control goes back to step 606 to process the next pixel.

After all pixels have been processed, control goes to step 616 which calculates the percentage of scar tissue in the mammary system of the animal.

The process of FIG. 6 may first separate the mammary system tissue from the other tissue in the scan before performing the steps starting with step 606.

Figure 7:
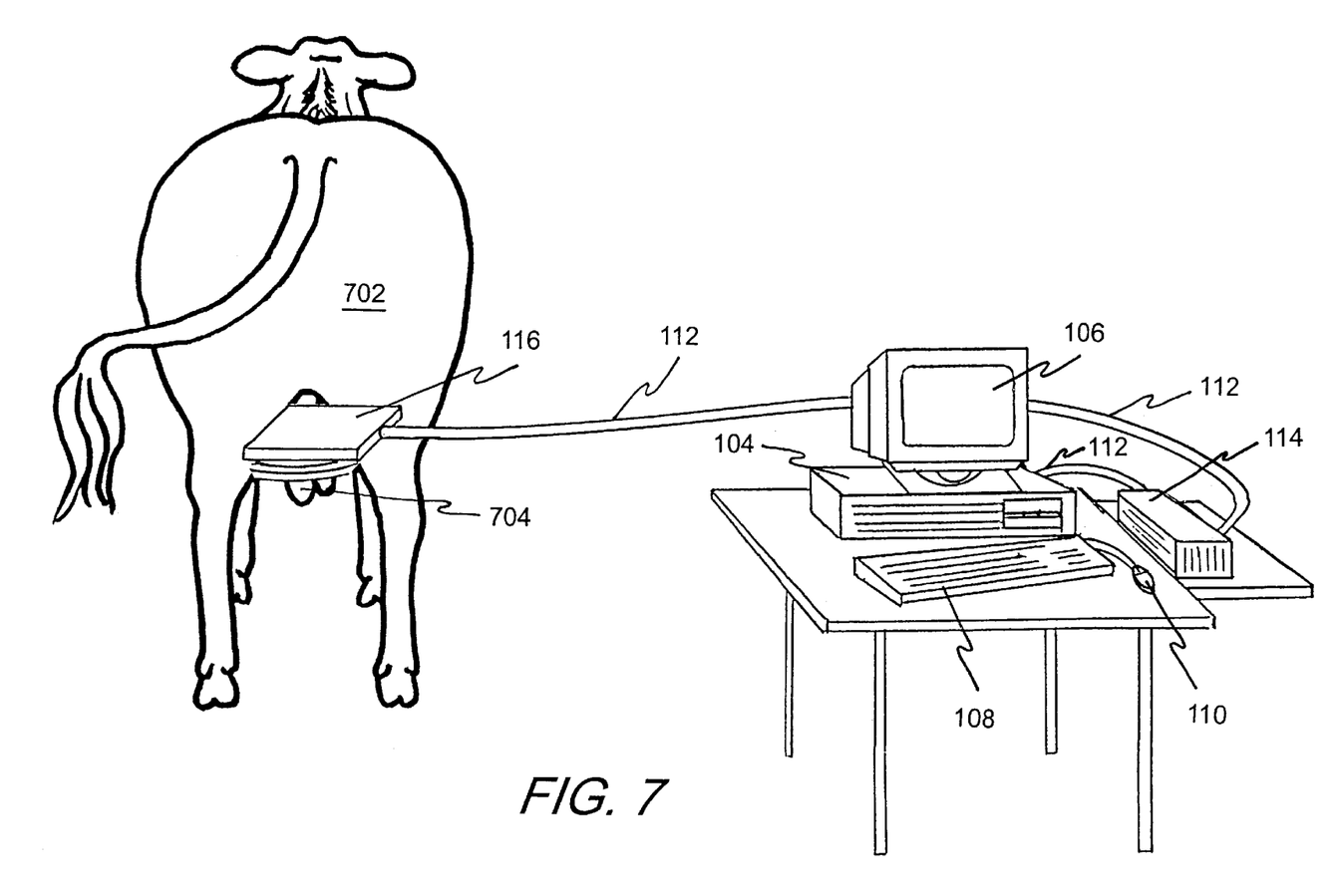
FIG. 7 shows a male animal (bull) being scanned to detect the testicles using the present invention.

FIG. 7 shows a male animal 702 being measured in the area of the testicles 704 using the present invention. Referring now to FIG. 7, the same measuring system as described in FIG. 1, is used to measure the testicles of a bull. The measuring system includes additional programs to detect the size of the testicles. FIG. 7 shows the present invention placing the scanning element 116 in position near the testicles 704 of the bull 702. The scanning element 116 could also be positioned to the side or in front of the testicles 704.

Figure 8A:
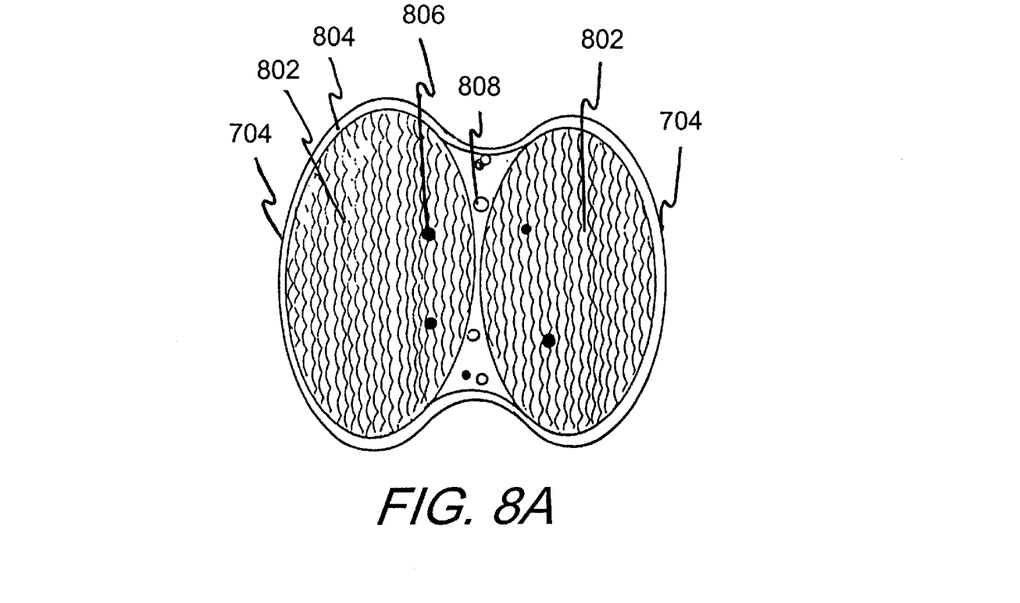
FIG. 8A shows a cross-section of the bull's testicles.
Figure 8B:
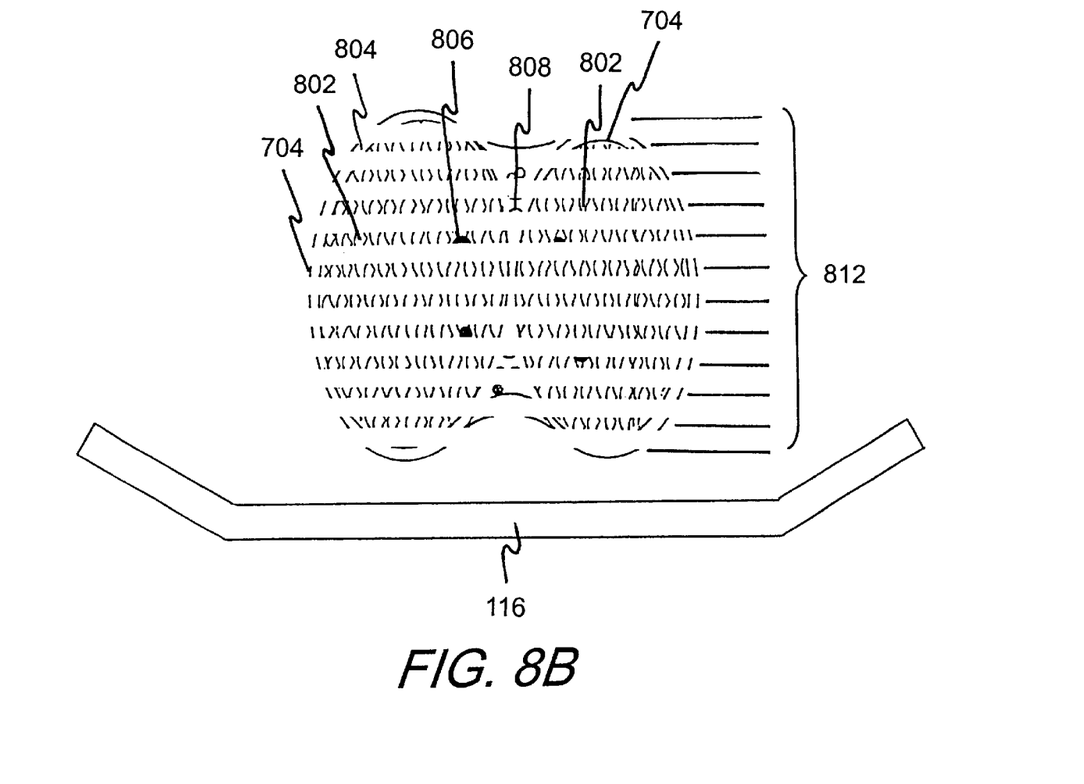
FIG. 8B shows MRI wave lines where an MRI scanner produces data of the size of testicles and the density of the sperm producing cells.

FIGS. 8A and 8B show a horizontal cross-sectional view, FIG. 8A, taken from the rear of the testicles 704 and illustrates the location, FIG. 8B, where the scan of the testicles is typically taken of a bull. Referring now to FIG. 8B, The MRI scan, created from the scanner 116, produces a plurality of scan wave lines 812 which capture data about the semen producing cells 802 which are located within the scrotum 804. The numerous semen producing sells 802 are located within both testicles along with numerous blood vessels 806. The vas deferens 808 delivers the semen from the testicle to the seminal vesicle (not shown).

Once the scan is complete, the computer system 104 analyzes the MRI wave lines to determine the surface area and circumference of both testicles 804 by combining the end of each wave line which is defined as the scrotum 804. The longest representative wave line is considered to be the diameter of the testicles. Each wave line 812 can be analyzed to determine the average size of the semen producing cells 802 and the density of those cells. After analyzing the data, the computer system 104 rates and classifies the animal's testicles to rank them and compare them to similar testicles of like kinds of animals.

Figure 9:
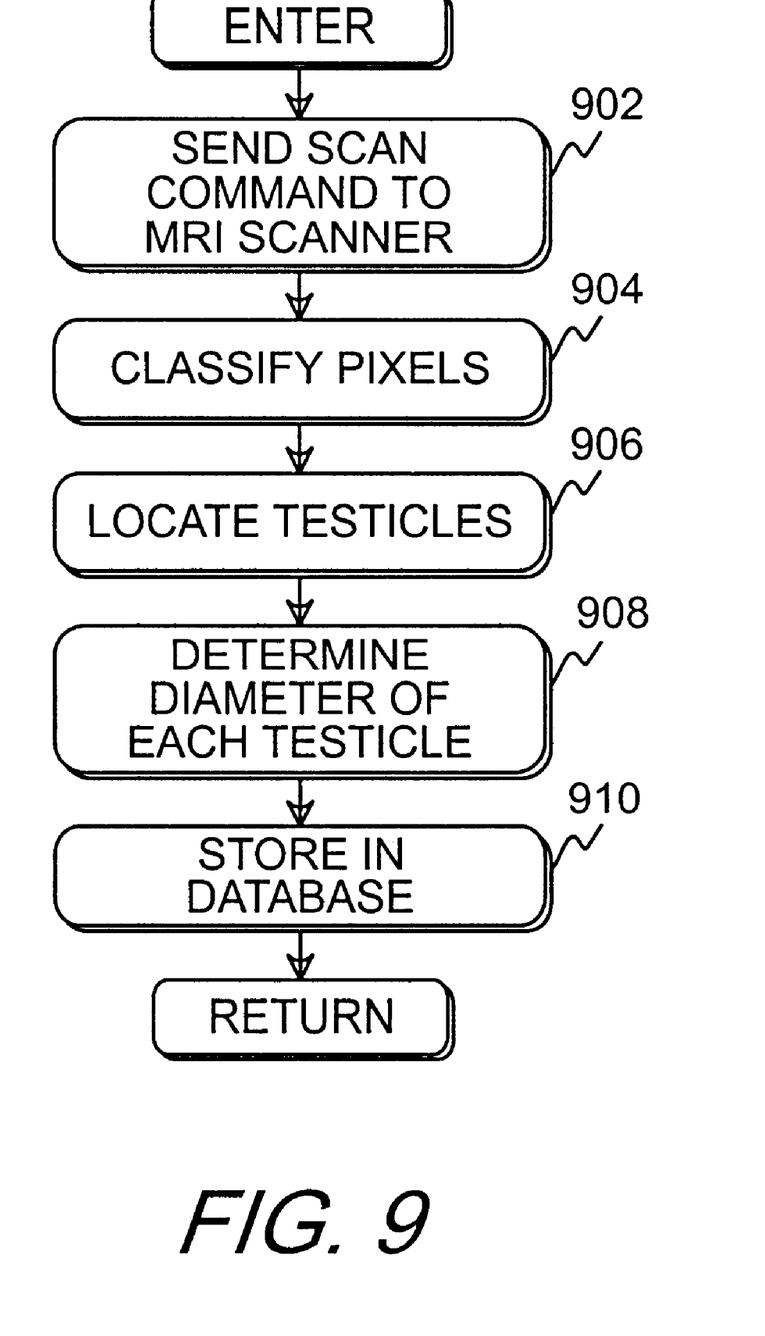
FIG. 9 shows a flowchart of the process of determining the size of the testicles of the animal shown in FIGS. 7, 8B and 8B.

FIG. 9 shows a flowchart of the process of determining the size of the testicles in the animal of FIGS. 7, 8A, and 8B.

Referring to FIG. 9, after entry, step 902 sends a scan command to the MRI scanner to cause it to perform a scan. The scanner has previously been placed at the back of the animal, in the vicinity of the animal's testicles, as shown in FIG. 7. After scanning, the scanner returns the scanned data, in the form of pixels of information, and step 904 classifies the pixels into various types of tissue based on the grayscale value of each pixel.

Once the pixels are classified, step 906 locates the testicles of the animal. Once the testicles are located, step 908 calculates the diameter of the testicles and the cross-sectional area of the testicles. Step 910 then stores this data in a database.

Having described a presently preferred embodiment of the present invention, it will be understood by those skilled in the art that many changes in construction and circuitry and widely differing embodiments and application of the invention will suggest themselves without departing from the scope of the present invention, as defined in the claims. The disclosures and the description here in are intended to be illustrative and are not in any sense limiting of the invention, defined in scope by the following claims.

What is claimed is:

1. A system for determining pregnancy of an animal, the system comprising:

a computer system;

a magnetic resonance imaging scanner connected to the computer system, and located adjacent an area of tissue of an animal to be scanned, wherein scan wave line data, produced by the scanner, is transferred to the computer system;

scan evaluation software located within the computer system for evaluating the wave line data produced by the scanner to locate the uterus of the animal, detect the presence of an embryo within the uterus, determine a size of the embryo, and determine pregnancy from the size of the embryo.

2. The system of claim 1 wherein a size of the embryo is compared to a size of an embryo of an animal of like kind and size to determine pregnancy.

3. The system of claim 1 wherein a size of the uterus is compared to a size of the uterus from a previous measurement of the animal to determine pregnancy.

4. The system of claim 1 further comprising:

a photographic output device connected to the MRI scanner to transfer scan wave lines to a photographic negative; and scanning the photographic negative to produce the scan wave line data.

5. The system of claim 1 further comprising classification software within the scan evaluation software to rank an embryo in the uterus within like kinds of animals.

6. The system of claim 1 wherein pregnancy is determined by locating bone tissue within a reproductive area of the animal.

7. The system of claim 1 further comprising the step of ranking the embryo within like kinds of animals.

8. A method for determining pregnancy of an animal by measuring tissue within the animal, the method comprising the steps of:

(a) locating a scanning element of a magnetic resonant imaging scanner adjacent to a reproductive area of tissue of the animal to be scanned;

(b) scanning a portion of the animal with the magnetic resonance imaging scanner;

(c) transferring scan wave line data, produced by the scanner, to a computer system;

(d) within the computer system, classifying each pixel within each line of the scan wave line data into a first class of pixel representing muscle tissue within the tissue scanned, and a second class of pixel representing other tissue within the tissue scanned;

(e) within the computer system, locating a pair of circular areas surrounded by muscle within the area scanned;

(f) selecting a smaller circular area of the pair of circular areas located in step (e) as a uterus;

(g) selecting a circular area of tissue within the uterus as an embryo;

(h) measuring an area of the embryo selected in step (g); and (i) comparing a size of the embryo measured in step (h) to a predetermined size and if the size of the embryo measured in step (h) is larger than the predetermined size, determining that the animal is pregnant.

9. The system of claim 8 wherein the predetermined size of the embryo is a size of an embryo of an animal of like kind and size.

10. The system of claim 8 wherein the predetermined size of the uterus is a size of the uterus from a previous measurement of the same animal.

11. A system for measuring scar tissue within an animal, the system comprising:

a computer system;

a magnetic resonance imaging scanner connected to the computer system, and located adjacent an area of tissue of an animal to be scanned, wherein scan wave line data, produced by the scanner, is transferred to the computer system;

scan evaluation software located within the computer system for evaluating the wave line data produced by the scanner to calculate and display a percentage of scar tissue within the tissue scanned by the scanner.

12. The system of claim 11 further comprising:

a photographic output device connected to the MRI scanner to transfer scan wave lines to a photographic negative; and scanning the photographic negative to produce the scan wave line data.

13. The system of claim 11 further comprising classification software within the scan evaluation software to rank the animal within like kinds of animals.

14. A method for measuring scar tissue within an animal, the method comprising the steps of:

(a) locating a scanning element of a magnetic resonant imaging scanner adjacent to a selected area of tissue of the animal to be scanned;

(b) scanning a portion of the animal with the magnetic resonance imaging scanner;

(c) transferring scan wave line data, produced by the scanner, to a computer system;

(d) within the computer system, classifying each pixel within each line of the scan wave line data into a first class of pixel representing normal tissue within the tissue scanned, and a second class of pixel representing scar within the tissue scanned;

(e) within the computer system, calculating a percentage of scar tissue within each scan wave line as a number of the second class of pixels divided by the sum of both the first class of pixels and the second class of pixels times one hundred; and (f) within the computer system, averaging the percentage of scar tissue of each of the scan wave lines and displaying this average as a percentage of scar tissue within the tissue scanned by the scanner.

15. The method of claim 14 wherein step (b) further comprises the steps of:

(b1) transferring scan wave line data from the magnetic resonance imaging scanner to a photographic medium; and (b2) scanning the photographic medium to produce the scan wave line data.

16. The method of claim 14 further comprising the step of:

(g) ranking the animal by percentage of scar tissue within like kinds of animals.

17. A system for measuring a size of an organ of an animal, the system comprising:

a computer system;

a magnetic resonance imaging scanner connected to the computer system, and located adjacent the organ to be measured, wherein scan wave line data, produced by the scanner, is transferred to the computer system;

scan evaluation software located within the computer system for evaluating the wave line data produced by the scanner to locate the organ of the animal, and determine a size of the organ.

18. The system of claim 17 wherein the organ being measured is a testicle of the animal.

19. The system of claim 17 wherein the organ being measure is the uterus of the animal.

* * * * *